(12) United States Patent
Whalen et al.

(10) Patent No.: US 9,655,503 B2
(45) Date of Patent: May 23, 2017

(54) DUAL SURFACE DENTAL DEVICE FOR USE IN INTRAORAL PHOTOGRAPHY

(71) Applicant: Lynn Whalen, Palm City, FL (US)

(72) Inventors: Lynn Whalen, Palm City, FL (US); Jenna Mackey, Port St. Lucie, FL (US)

(73) Assignee: Lynn Whalen, Palm City, FL (US)

( * ) Notice: Subject to any disclaimer, the term of this patent is extended or adjusted under 35 U.S.C. 154(b) by 0 days.

(21) Appl. No.: 14/106,400

(22) Filed: Dec. 13, 2013

(65) Prior Publication Data

US 2014/0170590 A1 Jun. 19, 2014

Related U.S. Application Data

(60) Provisional application No. 61/737,454, filed on Dec. 14, 2012.

(51) Int. Cl.
*A61B 1/247* (2006.01)
*A61B 6/14* (2006.01)

(52) U.S. Cl.
CPC ............... *A61B 1/247* (2013.01); *A61B 6/14* (2013.01)

(58) Field of Classification Search
CPC .............. A61B 1/24; A61B 1/247; A61B 6/14
USPC ................................ 433/30–31, 229; 396/16
See application file for complete search history.

(56) References Cited

U.S. PATENT DOCUMENTS

| | | |
|---|---|---|
| 252,127 A | 1/1882 | Morrill |
| 692,281 A | 2/1902 | Hare |
| 751,950 A | 2/1904 | Sharp |
| 1,540,409 A | 6/1925 | McCray |
| 2,336,392 A | 12/1943 | Burlo |
| D161,478 S | 1/1951 | Lundgren |
| 2,574,217 A | 11/1951 | Lundgren et al. |
| 2,723,661 A | 11/1955 | Hull |
| 2,809,430 A | 10/1957 | Barber |
| 3,031,930 A | 5/1962 | Kafig et al. |
| 3,151,395 A | 10/1964 | Moniot |
| 3,162,191 A | 12/1964 | Canan |
| 3,171,203 A | 3/1965 | Arroyo |
| 3,829,199 A | 8/1974 | Brown |
| 4,182,312 A | 1/1980 | Mushabac |
| 4,279,594 A | 7/1981 | Rigutto |
| 4,412,821 A | 11/1983 | Sturdivant |
| 4,512,635 A | 4/1985 | Melde |
| D281,622 S | 12/1985 | Diamond |
| 4,931,015 A | 6/1990 | Amadei |
| D319,503 S | 8/1991 | Summers |

(Continued)

FOREIGN PATENT DOCUMENTS

JP 61093404 * 5/1986 ............ G02B 5/08

*Primary Examiner* — Cris L Rodriguez
*Assistant Examiner* — Hao D Mai
(74) *Attorney, Agent, or Firm* — McHale & Slavin P.A.

(57) ABSTRACT

The present invention describes a dual sided dental instrument for use in intraoral photography. Each side of the dental instrument forms a different surface providing the user the capability to use a single device for differing functions. In a preferred embodiment, the dual sided dental instrument for use in intraoral photography preferably contains a first surface having reflective materials. Use of reflective materials provides a mechanism for the dentist or dental hygienist to photograph the inner portions of the patient's upper or lower teeth. The opposing side contains a surface which is adapted to provide background for intraoral images.

12 Claims, 13 Drawing Sheets

(56) References Cited

U.S. PATENT DOCUMENTS

| | | |
|---|---|---|
| 5,052,925 A | 10/1991 | Stalcup |
| 5,139,420 A | 8/1992 | Walker |
| D329,287 S | 9/1992 | Ziese |
| D344,335 S | 2/1994 | Elisha |
| D359,556 S | 6/1995 | Hale et al. |
| 5,458,486 A | 10/1995 | Ballard |
| D368,963 S | 4/1996 | Gomes |
| 5,528,432 A | 6/1996 | Donahoo |
| 5,656,014 A | 8/1997 | Rooney et al. |
| 5,951,284 A | 9/1999 | Lake |
| 6,319,004 B1 | 11/2001 | Forsline |
| D463,554 S | 9/2002 | Li |
| 6,837,707 B2 | 1/2005 | Figueredo Torres |
| 6,932,601 B2 | 8/2005 | Frider et al. |
| 7,021,798 B2 | 4/2006 | Tsimerman et al. |
| D535,394 S | 1/2007 | Johnson et al. |
| 8,182,264 B2 | 5/2012 | Dragan et al. |
| 2003/0076605 A1 | 4/2003 | Shohet |
| 2005/0026104 A1 | 2/2005 | Takahashi |
| 2005/0084826 A1 | 4/2005 | Pilaro et al. |
| 2006/0105288 A1 | 5/2006 | Garfinkel |
| 2006/0141415 A1* | 6/2006 | Johnson et al. ............... 433/30 |
| 2010/0190134 A1 | 7/2010 | Park |

* cited by examiner

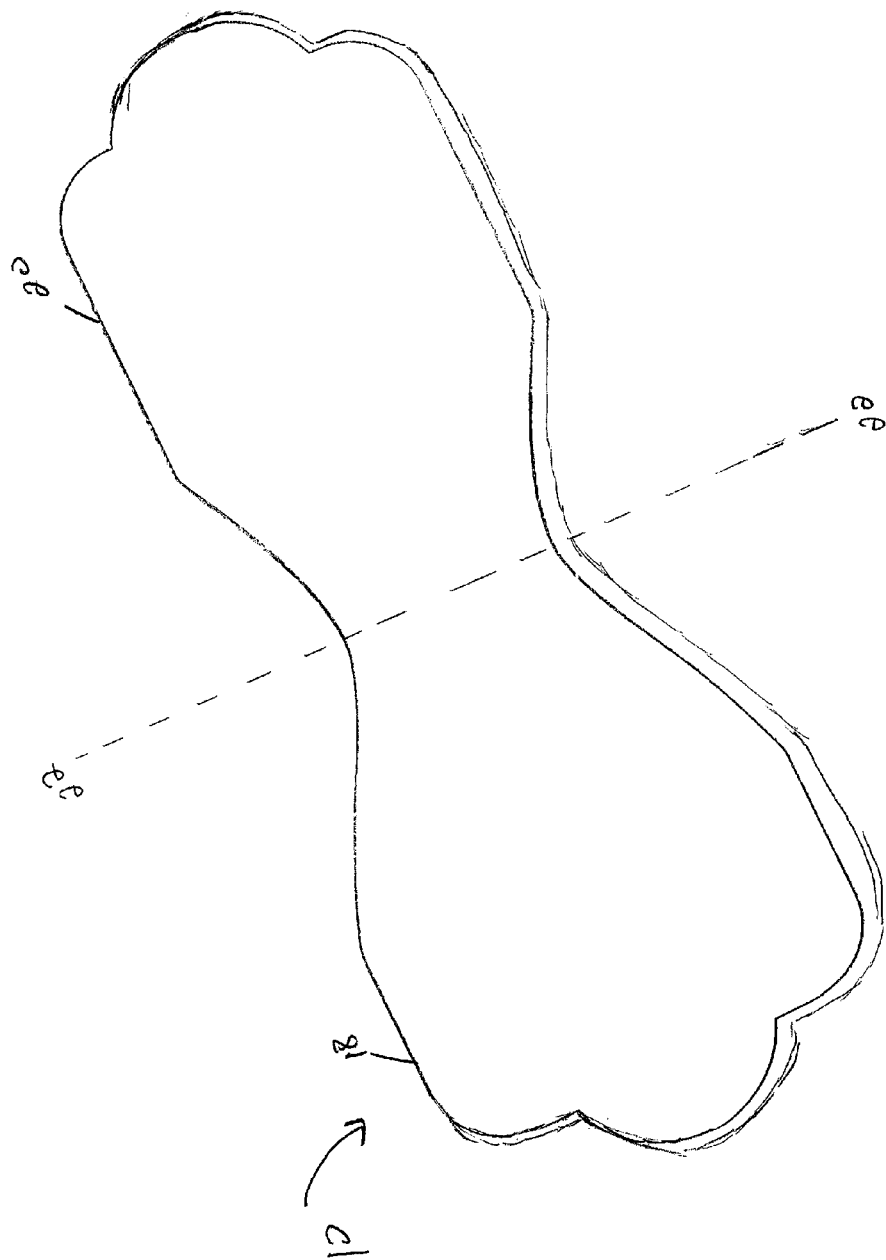

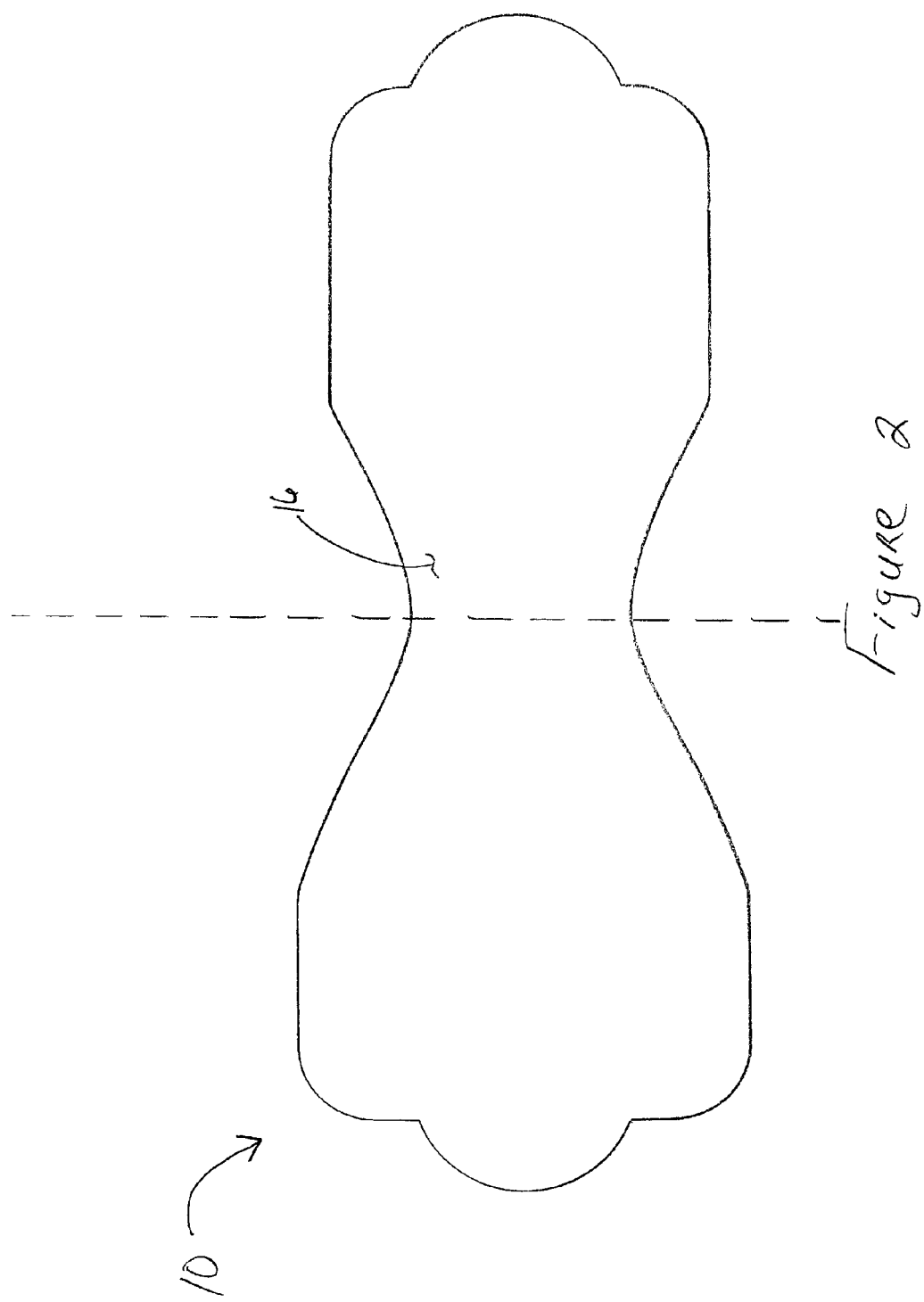

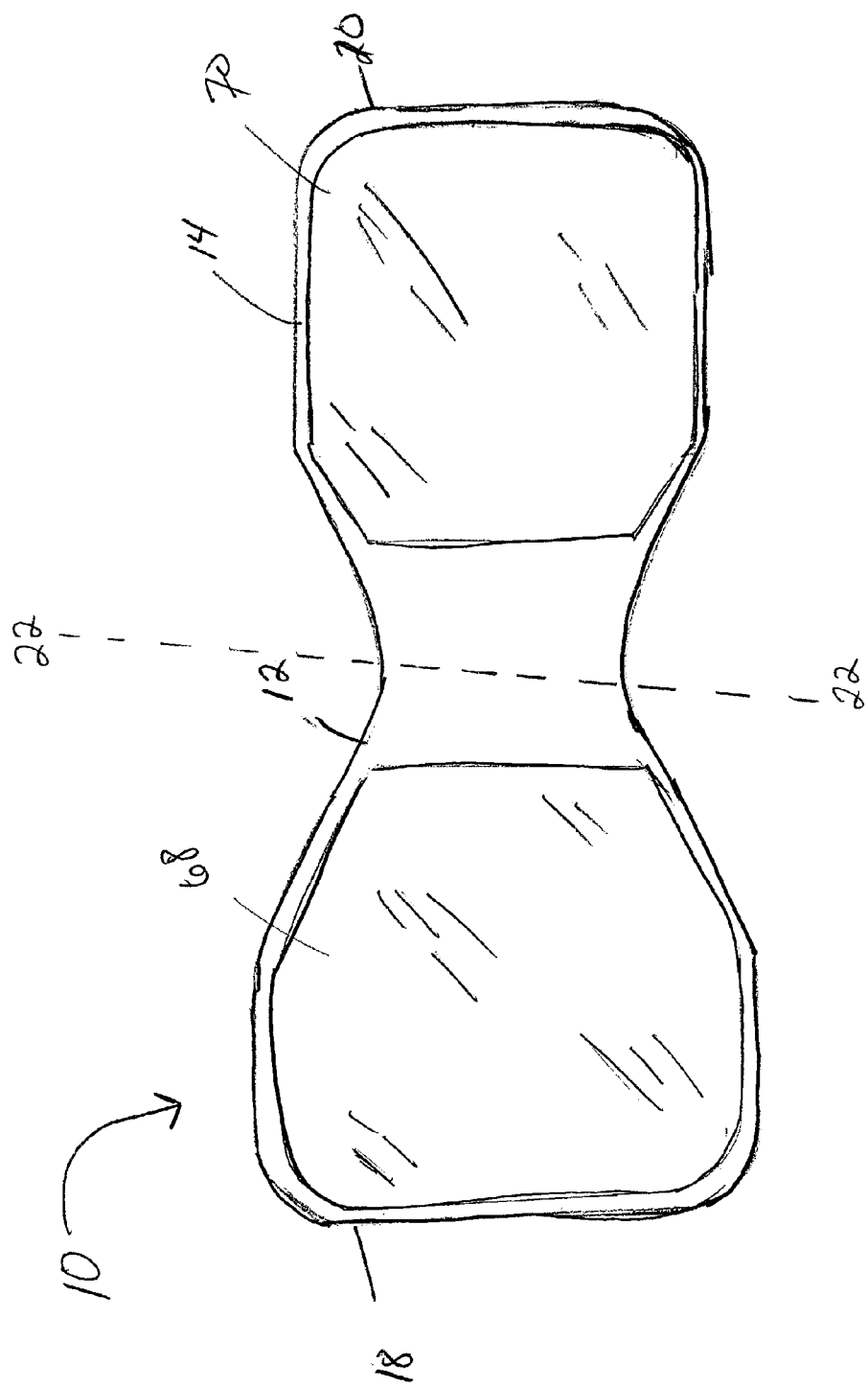

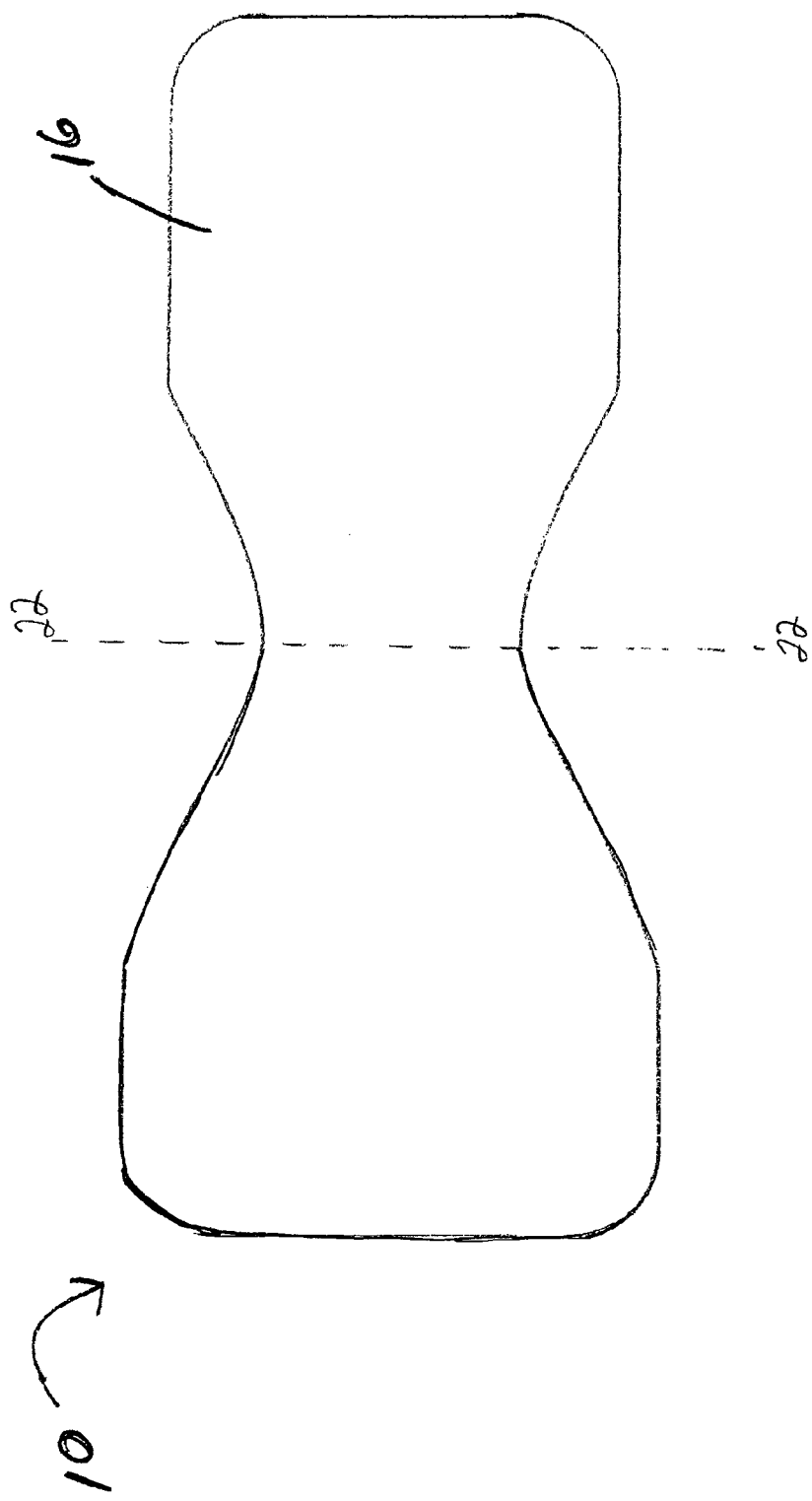

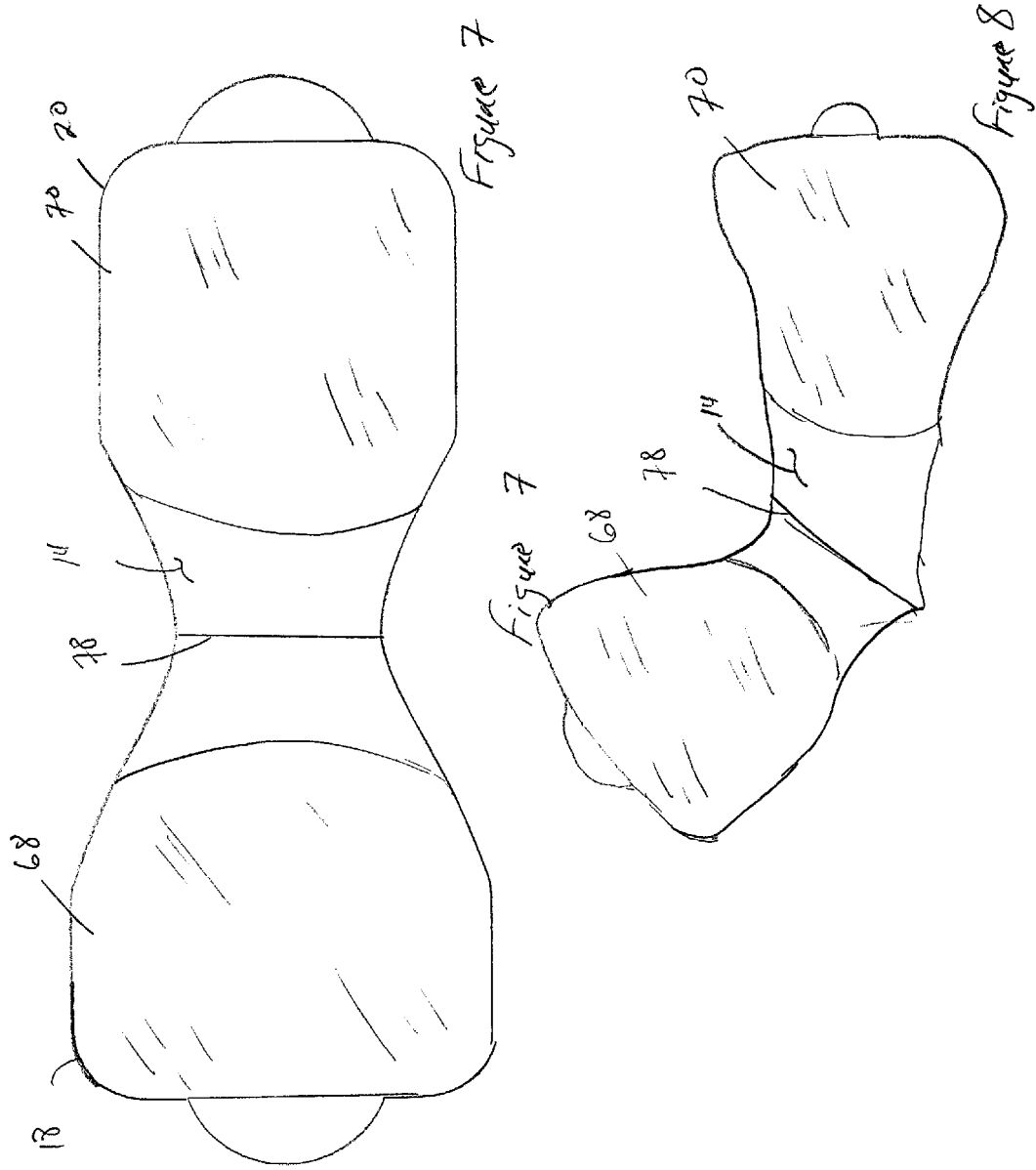

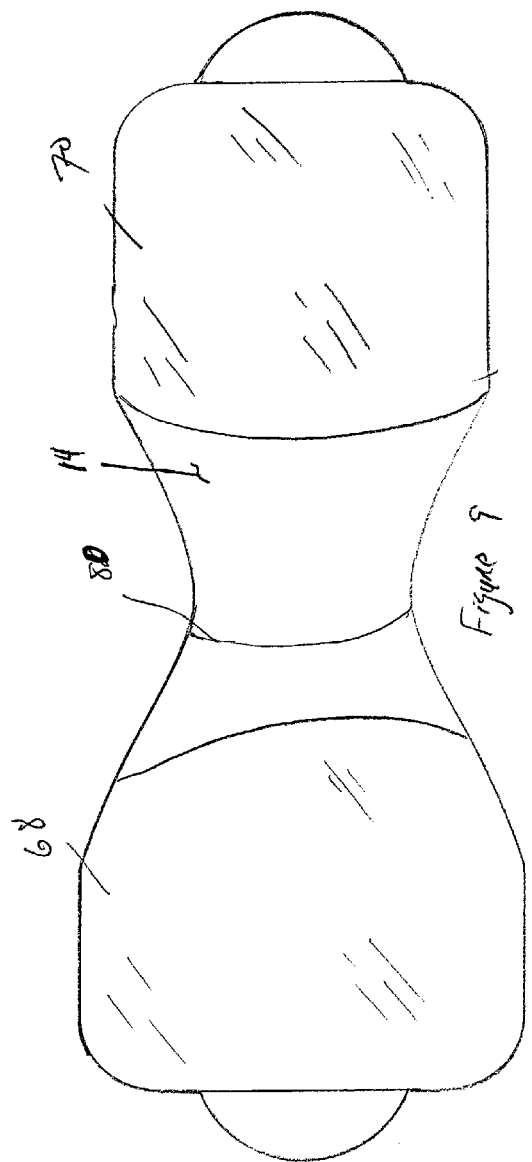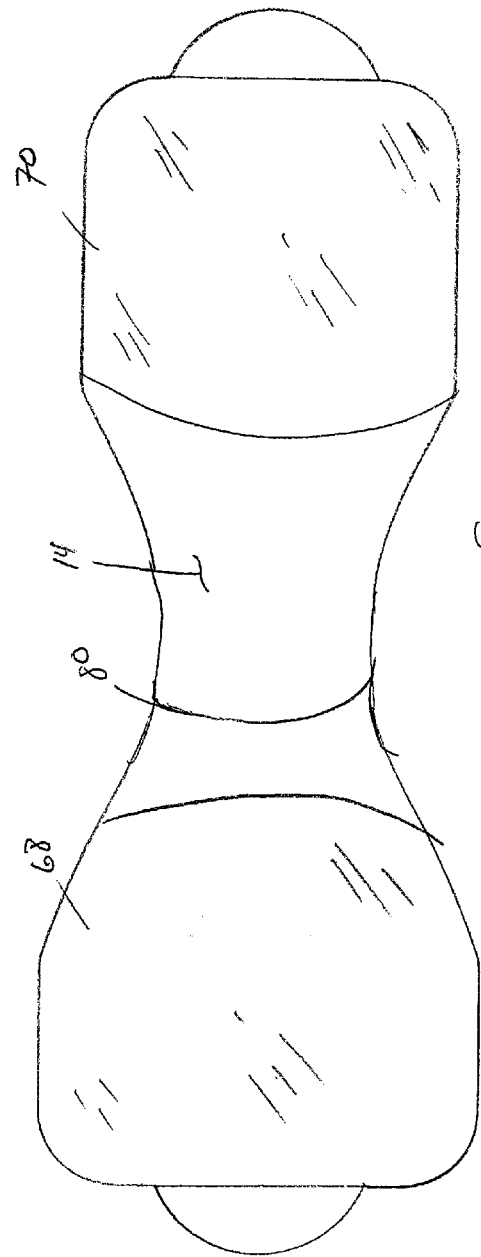

DUAL SURFACE DENTAL DEVICE FOR USE IN INTRAORAL PHOTOGRAPHY

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 61/737,454, filed Dec. 14, 2012, entitled "DUAL SURFACE DENTAL DEVICE FOR USE IN INTRAORAL PHOTOGRAPHY". The contents of the above referenced application is incorporated herein by reference.

FIELD OF THE INVENTION

The present invention relates to dental instruments; and more particularly to a dental instrument adapted for use in intraoral photography.

BACKGROUND OF THE INVENTION

Photography has played an increasing role in the dental field over the years. Typically, use of X-ray technology was the primary means of visualization of the teeth structure. While such technology is effective at illustrating to a patient various disease states, most patients fail to completely understand the information that a dentist may be trying to convey using an X-ray image. Use of digital cameras, in combination with display devices and/or printers, allows dentists and staff to easily and cheaply utilize photographic technology to enhance their practice. Such technology is crucial in modern dental offices in dealing with patients who increasingly expect instantaneous, visual results.

As dentistry moves away from disease based treatment options to more of an emphasis on appearance based treatment options, more established technologies like X-ray images fail to convey the necessary message in an effective manner. In making decisions for appearance based treatment options, use of photography and photographic images provide patients a powerful tool in the decision making process. In addition to photographic images being invaluable in communicating outward appearance of the patient's teeth, dental photography has been used to provide patient instruction, for legal reasons, for treatment planning, and as a liaison with laboratories.

DESCRIPTION OF THE PRIOR ART

Various dental tools have been used to aid the dentist and/or staff in diagnosing, cleaning, or for providing appearance enhancement. For example, U.S. Pat. No. 8,182,264 describes a dental bite block. The dental bite block is described as a sheet of material having a central body portion with attached wings capable of folding towards each other on either side. The wings of the bite block fold toward each other along fold lines adjacent the central body portion and provide a structure for biting down upon for propping the mouth of a patient open during a dental procedure. A mirrored surface may be placed on the central body portion for improving visibility in the mouth.

U.S. Pat. No. 7,021,798 is described as relating to mirrors for use in confined spaces which are subject to being covered by fluids and debris, principally dental mirrors, for use by dentists and similar medical professionals. The mirror assembly includes a head portion and a handle portion. The head portion includes a housing with a rotor assembly and a rotor drive means. In accordance with the invention, a secondary member has a reflective surface. The mirror assembly includes attachment means for removably attaching the secondary member with respect to the rotor assembly so that the reflective surface can be replaced when degraded.

U.S. Pat. No. 6,837,707 describes a double dental mirror. The double dental mirror is described as provided with a multi-angular view of a working area and comprising a first mirror; a second mirror; and a bridge section. The bridge section is further described as forming at least one of an angle and an arch. The configuration of the dental mirror is described as providing the dental practitioner with multiple views of the working area, and at the same time, provides an enlargement of the working area by isolating the tongue and cheeks from the working area.

U.S. Pat. No. 5,951,284 describes an intraoral instrument. The intraoral instrument is described as a double-sided mirror and irrigation instrument for intraoral application having an in-line finger operated valve for selectively controlling flow of air, water or a mixture of air and water through an annular supply passage for cleaning the mirror surfaces and objects in the oral cavity. An annular suction passage extends from the mirror assembly through an extension tube for draining liquids from the patient's mouth. The mirror assembly is illuminated by light transmitted through a quartz rod that is enclosed within a central supply conduit.

U.S. Pat. No. 3,829,199 describes a disposable dental mirror. The disposable dental mirror is described as comprising a plastic base adapted to hold a mirror thereon, the base having on its back side a receiving aperture to provide a removable frictional attachment between the base and a stem from a conventional dental mirror handle; and a mirror attached to the front surface of the base. The disposable mirror greatly minimizes cross-contamination between patients as it is inexpensive and may be conveniently discarded after use.

United States Patent Application Publication Number 2010/0190134 describes a lip retractor for intraoral photography. The lip retractor for intraoral photography is described as including a rectangular lip retracting member; and a handle formed on one side of the lip retracting member and having a slope of a predetermined degree, the handle including an air path and an air injection hole (formed on the inside thereof to thereby inject air to a miller during intraoral photography. The lip retractor for intraoral photography can more easily and conveniently retract the lips with one hand during intraoral photography and prevent frost formed on a miller by the steam of breath to thereby obtain a clearer image.

United States Patent Application Publication Number 2006/0105288 describes a dental mirror for aligning dental implants. The mirror is described as useful for a periodontist that includes indicia alignment and spacing on the mirror at a predetermined location that provides for manual alignment of a drill that can be used by the periodontist for drilling an accurately aligned hole for a dental implant while holding the mirror in one hand observing the indicia and holding the drill in the other hand. The mirror is also described as useful by a dentist, periodontist and orthodontist to allow better patient access to facilitate looking at various teeth and gum areas in a patient's mouth by providing mirror peripheral shapes that fit lip, tongue and areas between the cheek and gums.

United States Patent Application Publication Number 2005/0026104 discloses an intraoral camera system. The intraoral camera system is described as including a dental mirror having an aperture for transmitting light there-through, the aperture being provided in the center or any other part of the mirror by removing a reflective material therefrom. The system is further described as having a CCD camera secured on a back surface of the dental mirror in such a manner that the aperture coincides with its incident portion. A hand mirror shaped monitor may also be provided for displaying image data received from the CCD camera via cable or radio, and a server is also provided that is capable of storing and outputting the image data any time onto the monitor, wherein even though a patient is laid down on a chair in a horizontal position, the patient or a third party can utilize the hand mirror shaped monitor to view an image which is very close to the image that a dentist views through reflection from the dental mirror having said CCD camera built therein.

United States Patent Application Publication Number 2003/0076605 describes a mirror. The mirror is described as comprising a handle portion unitary with a mirror-head portion including reflective or mirror surfaces on opposing surfaces of the mirror-head portion. The mirror includes an anti-fog material coated onto the mirror surfaces to prevent the formation of condensation on the mirror surfaces. The mirror is described as including an indicator to inform an operator that the mirror has been used and should be disposed of appropriately. The mirror is further described as being disposable, can be prepackaged and/or pre-sterilized to provide better results and a predictably cleaner instrument, and can be designed to prevent use of the mirror on more than a single subject.

SUMMARY OF THE INVENTION

The present invention describes a dual sided dental instrument for use in intraoral photography. Each side of the dental instrument forms a different surface providing the user the capability to use a single device for differing functions. In a preferred embodiment, the dual sided dental instrument for use in intraoral photography preferably contains a first surface having reflective materials. Use of reflective materials provides a mechanism for the dentist or dental hygienist to photograph the inner portions of the patient's upper or lower teeth. The opposing side contains a surface which is adapted to provide background for intraoral images.

Accordingly, it is an objective of the present invention to teach a multi-functional dental instrument.

It is a further objective of the present invention to teach a multi-functional dental instrument adapted for use in intraoral photography.

It is yet another objective of the present invention to teach a multi-functional dental instrument adapted for use in visualizing anatomical features inside of the mouth.

It is a still further objective of the invention to teach a multi-functional dental instrument adapted to enhance intraoral photographic images.

It is a further objective of the present invention to teach a multi-functional dental instrument adapted for use in intraoral photography and visualization anatomical features inside of the mouth.

It is a still further objective of the invention to teach a dental instrument which contains two different surfaces which are useful in intraoral photography and is easily manufactured.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 1C is a perspective view of the dual sided dental instrument shown in FIG. 1A;

FIG. 2 is a rear view of the dual sided dental instrument for use in intraoral photography illustrated in FIG. 1;

FIG. 3 is a front view of an alternative embodiment of a dual sided dental instrument for use in intraoral photography in accordance with the present invention;

FIG. 4 is a rear view of the dual sided dental instrument for use in intraoral photography illustrated in FIG. 3;

FIG. 7 is an alternative embodiment of the dual sided dental instrument for use in intraoral photography, illustrated having a hinged portion;

FIG. 8 illustrates the dual sided dental instrument for use in intraoral photography shown in FIG. 7 in a hinged position;

FIG. 9 is an alternative embodiment of the dual sided dental instrument for use in intraoral photography having length expansion functionality;

FIG. 10 illustrates the dual sided dental instrument for use in intraoral photography shown in FIG. 9 in the expanded position;

DETAILED DESCRIPTION OF THE INVENTION

Figure 1A:
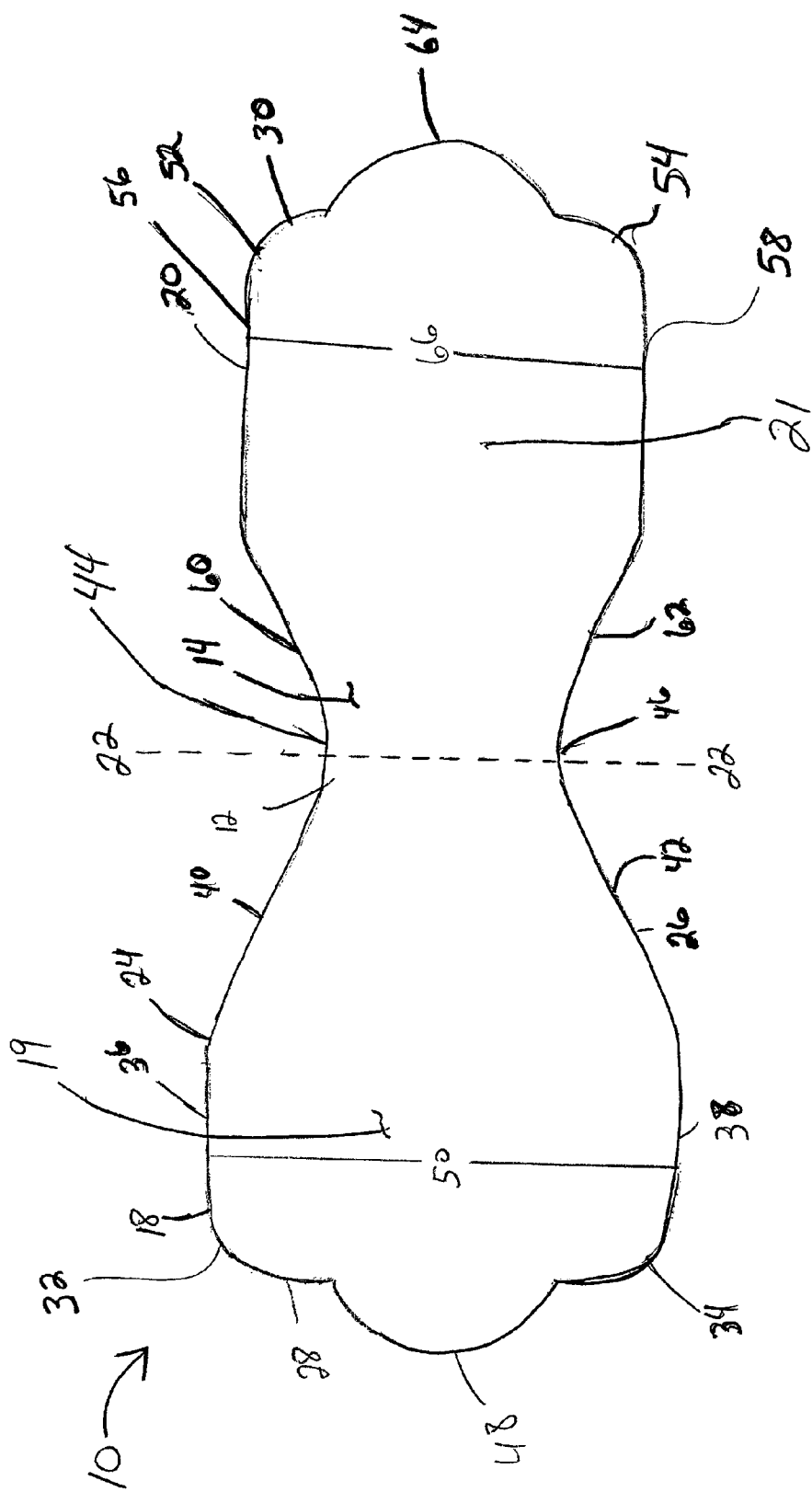
FIG. 1A is a top view of an illustrative embodiment of a dual sided dental instrument for use in intraoral photography in accordance with the present invention shown without a reflective material.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring to FIGS. 1A-1G and FIG. 2, an illustrative embodiment of a dual sided dental instrument for use in intraoral photography, referred to generally as 10, is shown. The dual sided dental instrument 10 contains a generally planar main body 12 having a first surface 14 and an opposing second surface 16 (see FIG. 2). The main body 12 consists of a first end portion 18 which defines a first usable surface 19, a second end portion 20 which defines a second usable surface 21, and a transverse center axis 22. The dual sided dental instrument 10 is constructed and arranged so that the first end which defines a first usable surface 19 has generally the same geometrical shape or outline as the second end 20 which defines a second usable surface 21, differing however, in the size. Accordingly, the generally planar main body 12 contains a first end portion that is larger than a second end portion arranged oppositely about its transverse axis. Preferably, the dual sided dental instrument 10 is constructed as a single unit. However, the first end 18 and the second end 20 may be constructed independently and secured together using chemical fastening, heat sealing, or other mechanisms known to one of skill in the art.

The main body 12 is defined by two longitudinally opposing side edges, a first longitudinal side edge 24 and a second longitudinal side edge 26, and two vertically opposing side edges, a first vertical side edge 28 and a second vertical side edge 30. Each of the longitudinally opposing side edges 24, 26 and the two vertically opposing side edges 28 and 30 define the first end portion 18 and the second end portion 20. Referring back to FIG. 1, the first longitudinal side edge 24 and the second longitudinal side edge 26 which define the first end portion 18 are shaped to fit within the mouth of a human patient. The first longitudinal side edge 24 and the second longitudinal side edge 26 preferably contain opposing rounded or curved edges 32 and 34 which prevent damage to the internal structures of the patient's mouth when the device 10 is inserted therein.

At one end of the rounded or curved edges 32 and 34, a portion of the first longitudinal side edge 24 and the second longitudinal side edge 26 forms a generally straight line edge 36 and 38, thereby providing the first portion with a partial rectangular shape. The straight line edges 36 and 38 terminate in a generally inwardly angled edge 40 and 42. The inwardly angled edges 40 and 42 form an arcuate indentation 44 and 46 at about the transverse center axis 22. The opposite ends of the curved edges 32 and 34 form part of the first vertical side edge 28. Preferably, the dual sided dental instrument 10 contains a protuberance 48 along the first vertical side edge 28. However, such features may be omitted, see FIGS. 3 and 4. While the protuberance 48 is illustrated having a semi-circular shape, such shape can be varied as long as it functions to prevent the user's tongue from interfering with the intraoral photography when the device 10 is inserted therein. The distance between the first longitudinal side edge 24 and the second longitudinal side edge 26 along the first end portion 18 defines a length 50.

As described previously, the second end portion 20 forms generally the same shape as the first end portion 18, differing in size. Having dual portions that function the same but differ in size allows the user to easily and quickly use the device 10 for patients having different sized mouth structures without the need of having to use multiple, independently sized devices. Such feature also minimizes the space taken up by equipment used by the dentist or dental hygienists while performing dental procedures. Accordingly, the first longitudinal side edge 24 and the second longitudinal side edge 26 contain opposing rounded or curved edges 52 and 54.

At one end of the rounded or curved edges 52 and 54, a portion of the first longitudinal side edge 24 and the second longitudinal side edge 26 forms a generally straight line edge 56 and 58, thereby providing the second end portion with a partial rectangular shape. The straight line edges 56 and 58 terminate in a generally inwardly angled edge 60 and 62. The inwardly angled edges 60 and 62 form a portion of the arcuate indentations 44 and 46. The opposite ends of the curved edges 52 and 54 form part of the first vertical side edge 30. Preferably, the dual sided dental instrument 10 contains a protuberance 64 along the second vertical side edge 30. However, such features may be omitted, see FIGS. 3 and 4. While the protuberance 64 is illustrated having a semi-circular shape, such shape can be varied as long as it functions to prevent the user's tongue from interfering with the intraoral photography when the device 10 is inserted therein. The distance between the first longitudinal side edge 24 and the second longitudinal side edge 26 along the second end portion 20 defines a length 66. The length 66 along most of the first longitudinal side edge 24 and the second longitudinal side edge 26 is preferably smaller than the length 50 associated with the corresponding portions along the first end 18.

Figure 1B:
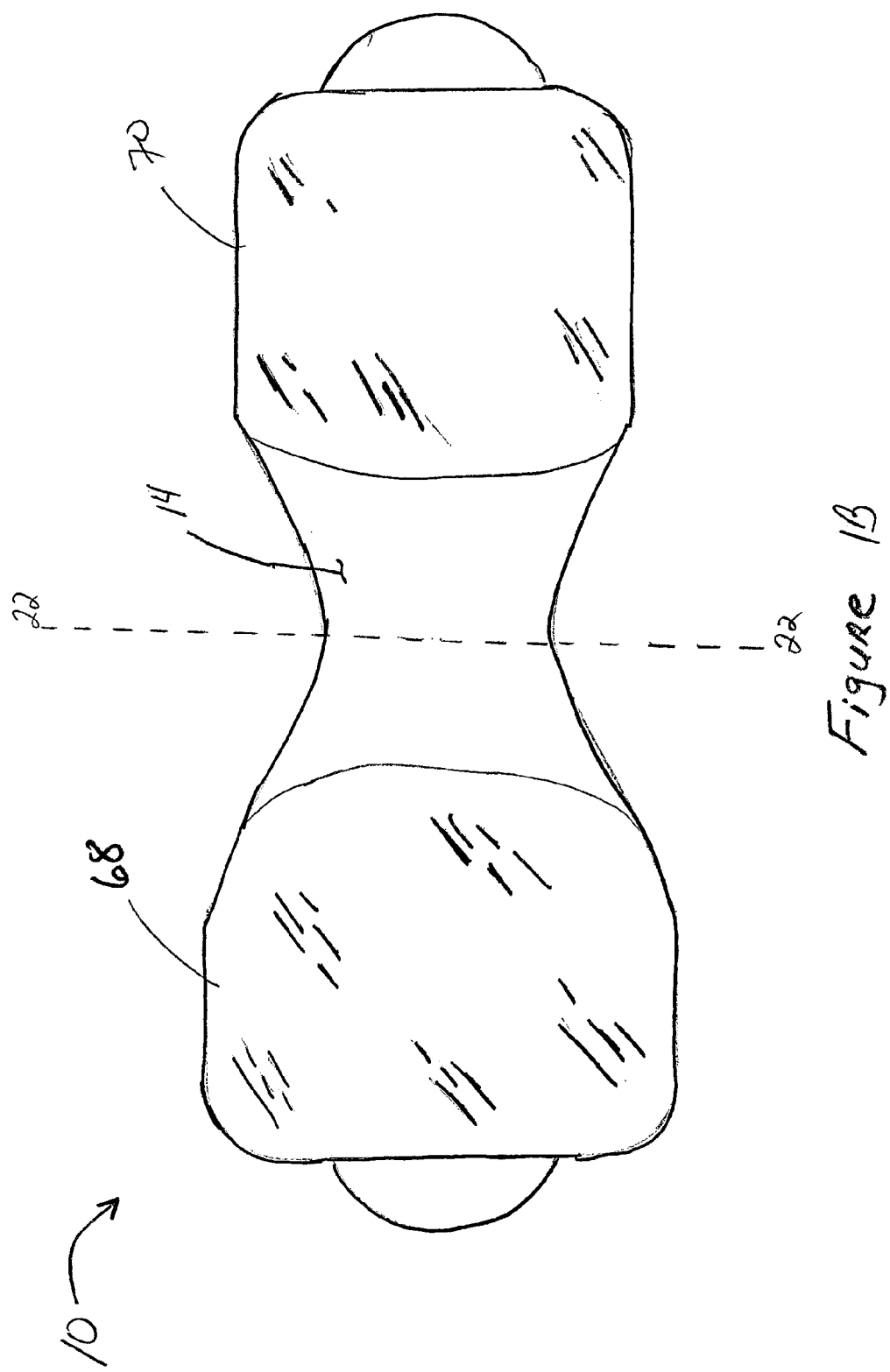
FIG. 1B is a bottom view of the dual sided dental instrument for use in intraoral photography in accordance with the present invention shown with reflective materials.
Figure 1E:
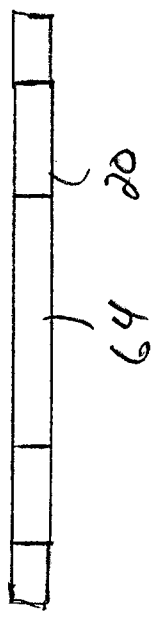
FIG. 1E is a front view of an alternative side of the dual sided dental instrument shown in FIG. 1A.
Figure 1D:
FIG. 1D is a front view of a first side of the sided dental instrument shown in FIG. 1A.
Figure 1F:
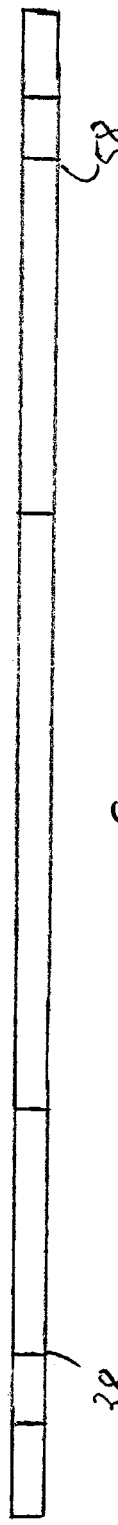
FIG. 1F is a side view of the dual sided dental instrument shown in FIG. 1A.
Figure 1G:
FIG. 1G is an alternative side view of the dual sided dental instrument shown in FIG. 1A.

Referring to FIG. 1B, the dual sided dental instrument 10 is illustrated with reflective materials attached to both the first end portion 18 and the second end portion 20. As shown, the reflective materials are illustrated as a first mirror 68 and a second mirror 70. Each mirror 68 and 70 is secured to at least a segment of the first end portion 18 and the second end portion 20 by any means known to one of skill in the art, including but not limited to chemical fastening, such as glue. The reflective material may be a thin adhesive coating with mirror like properties so that images of teeth can be reflected onto the dual sided dental instrument 10 with such clarity that all structures and features, both normal and diseased, can be captured by a camera. Additionally, nickel or chrome based substances can be added to the front surface 12 at appropriate places to produce mirror like image capability. In a preferred embodiment, the dual sided dental instrument 10 is made of a plastic or plastic resin like material. Preferably, the material allows the device to be sterilized using cold-sterilized techniques. Coupling, adhering, or securing the mirror, mirror like adhesive, or other substances like nickel or chrome can be accomplished using techniques known to one of skill in the art. Since the dual sided dental instrument 10 is designed to have flexibility particularly at or near the transverse axis 22, the coupling, adhering, or securing should be sufficient so that as the device 10 is bent or flexed, the mirror, mirror like adhesive, or other substances like nickel or chrome remain affixed thereto.

Figures 5A, 5B:
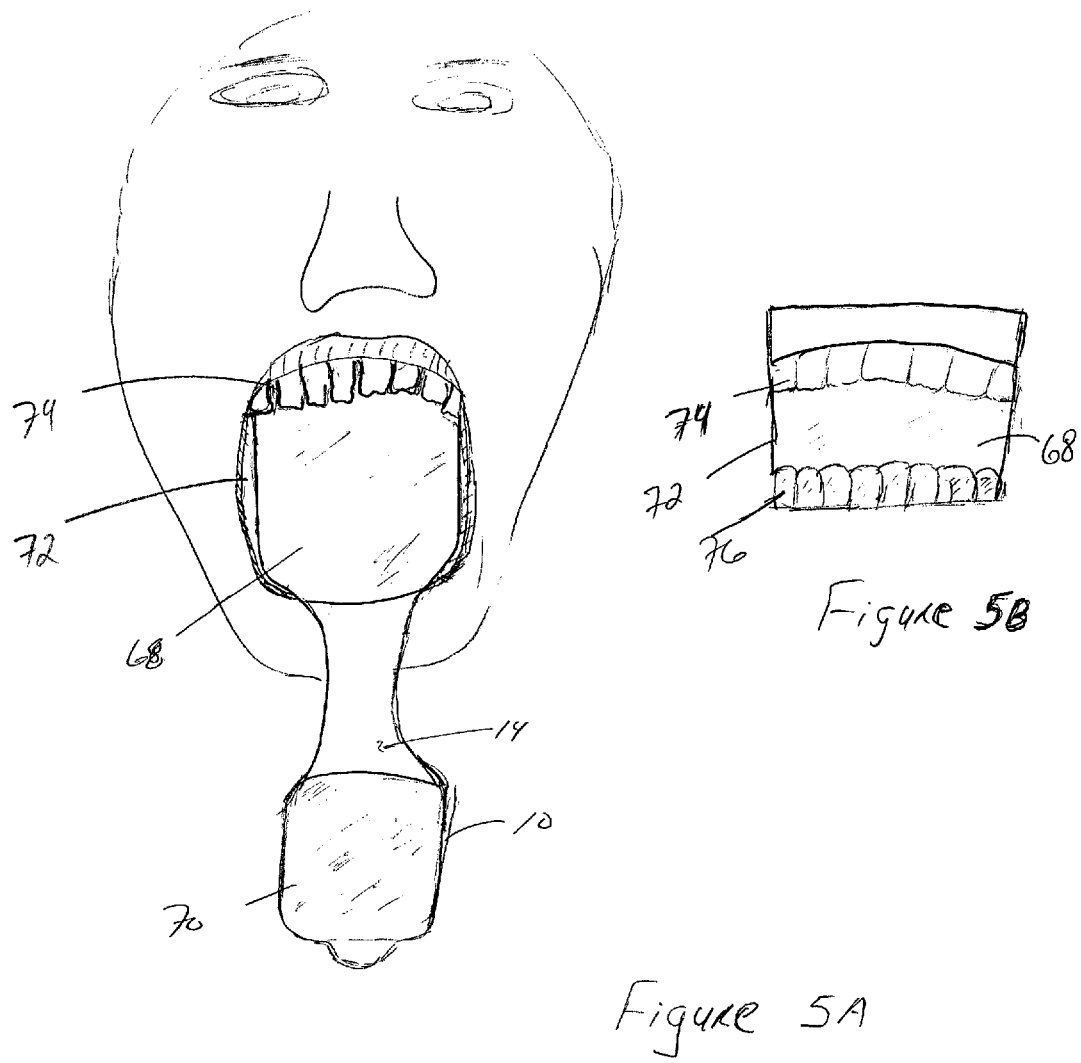
FIG. 5A is a perspective view of an illustrative embodiment of the dual sided dental instrument with the first reflective surface facing up when inserted within the mouth of a patient.
FIG. 5B illustrates the view of the teeth obtained when the dual sided dental instrument is inserted in the patient's mouth with the orientation shown in FIG. 5A.

In use, the dual sided dental instrument 10 is inserted within the patient's mouth 72 with the mirrors 68 and facing up towards teeth 74, see FIG. 5A. The shape and contour of each portion 18 or 20 is preferably designed to contour the shape of a human mouth. While the first end portion 18 is inserted therein, should the dentist need a smaller size, the dual sided dental instrument 10 is reversed so that the second end portion 20 is inserted into the mouth. As described above, the rounded corners prevent damage to the patient's mouth when the device 10 is inserted therein. The dual sided dental instrument 10 is positioned so the dentist or dental hygienist can capture images of the inner surfaces 76 of the teeth 74 which are reflected onto the mirrors 68 and 70. The images reflected onto the mirrors 68 or 70 are used to obtain various photographic images of the teeth 74.

Figure 6A:
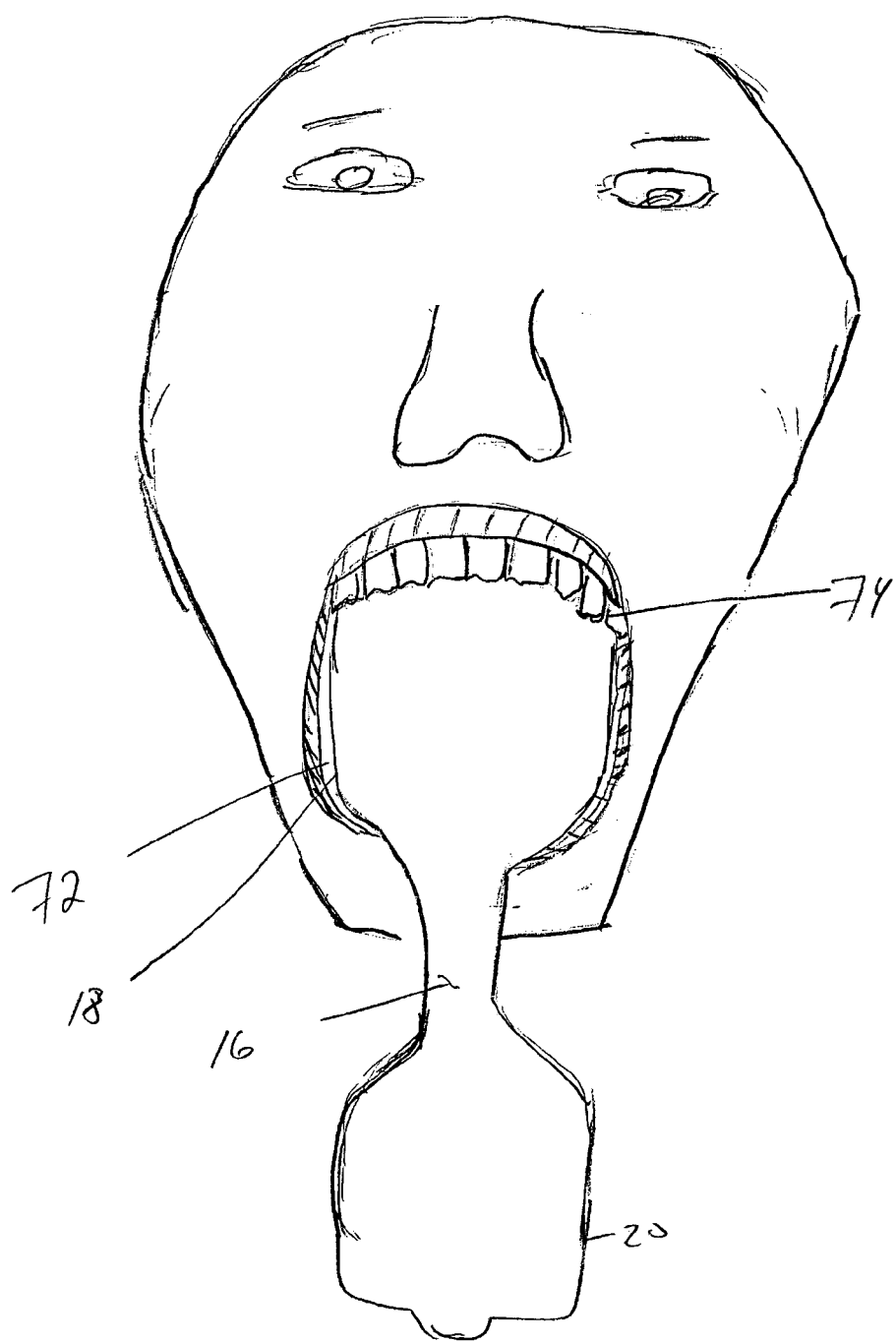
FIG. 6A is a perspective view of the dual sided dental instrument with the second surface facing up when inserted within the mouth of a patient.
Figure 6B:
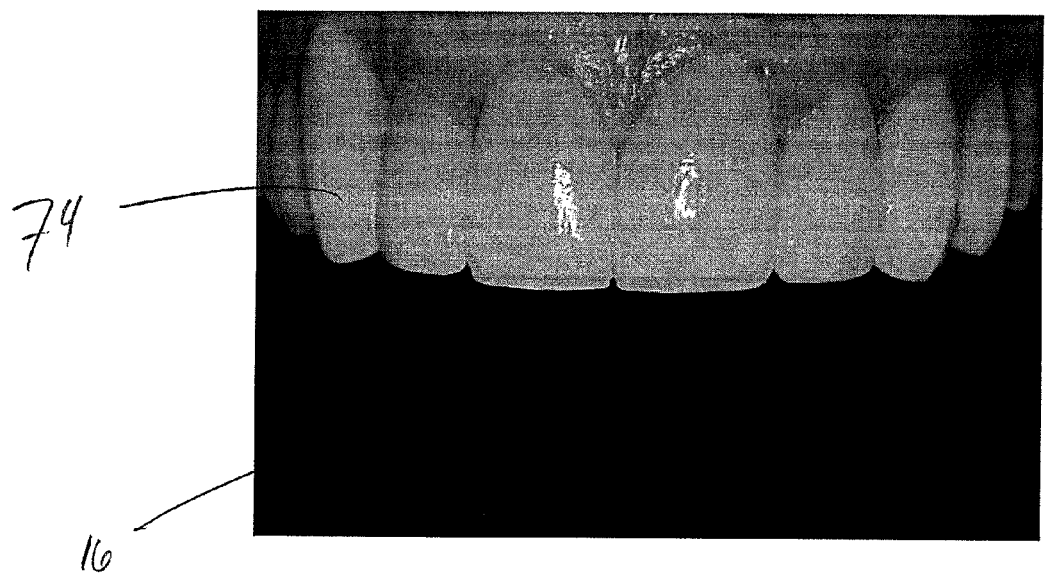
FIG. 6B illustrates the enhanced photographic functionality when the dual sided dental instrument is inserted in the patient's mouth with the orientation shown in FIG. 6A.

Referring to FIG. 2, the opposing second surface 16 is shown. The opposing second surface 16 is adapted to provide enhanced features when used in oral photography. As illustrated in FIG. 6A, when the dual sided dental instrument 10 is inserted within the patient's mouth with opposing second surface orientated in a face up position, a black background is produced. The black background, see FIG. 6B, allows for better contrast and visualization of the teeth structures. Such feature allows better communication regarding various characterizations of the teeth, such as colorization, conveyed to the patient and/or laboratories. In a preferred embodiment, the black background is produced by manufacturing the dual sided dental instrument 10 of a plastic material that provides a black matte finish. Alternatively, a thin film of material having a dark, preferably black, matte finish could be secured to the opposing second surface 16.

Referring to FIGS. 7-11, alternative embodiments of the dual sided dental instrument 10 are shown. In FIGS. 7-8, the dual sided dental instrument 10 is shown with partial or full bendability. To accomplish such functionality, the first end portion 18 and the second portion 20 contain a hinge, illustrated herein as a living hinge 78 which is positioned at or near the transverse center line 22. This allows the first end portion 18 to pivot about the hinge 78. Alternative hinged mechanisms know to one of skill in the art may be utilized, particularly if the dual sided dental instrument 10 is adapted so that at least one portion 18 or 20 can pivot relative to the other portion at least 90 degrees in a plurality of directions. In addition, the dual sided dental instrument 10 may further be adapted so that as the first end portion 18 moves up or down relative to the second end portion 20, the first portion 18 remains locked in its orientation.

Figure 11:
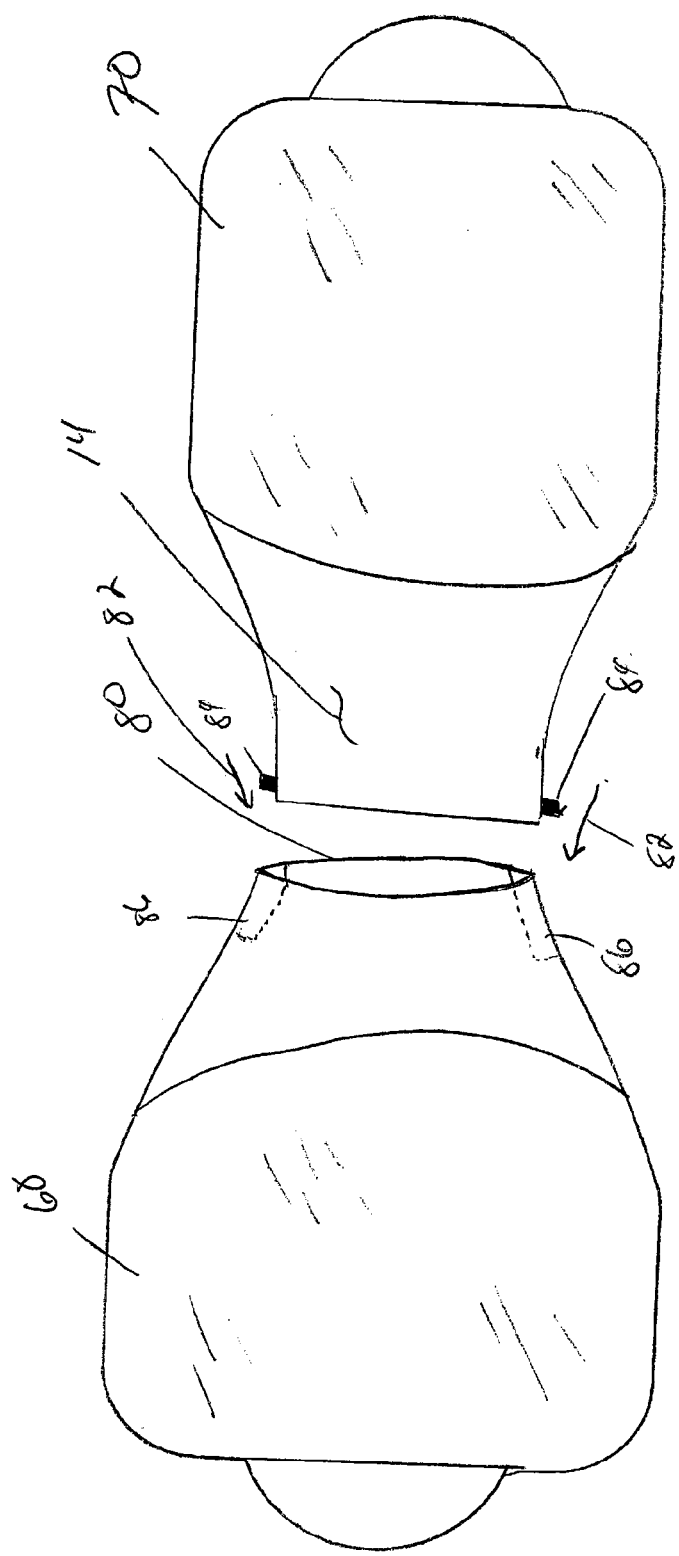
FIG. 11 is an exploded view of the dual sided dental instrument for use in intraoral photography shown in FIG. 9.

FIGS. 9-11 illustrate an alternative embodiment of the dual sided dental instrument 10 which is adapted to provide length extension. For example, should the user need the dual sided dental instrument 10 to extend from a first resting position, see FIG. 9, to a second extended position, see 10, the user simply pulls the first end 18 away from the second end 20. In this embodiment, the first end portion 18 is adapted to fit within an open end 80 of the second end portion 20, see arrows 82 in FIG. 11. In an illustrative example, the first end portion 18 may include one or more pins 84 adapted to fit into a channel or recessed portions 86 positioned within the second end portion 20. Sliding the pin 84 along the channel 86 allows for the overall length of the dual sided dental instrument 10 to increase or decrease.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A dual sided dental instrument for use in intraoral photography comprising:
    a planar main body having a first side adapted to provide a reflective side and an opposing second side adapted to provide a non-reflective side;
    said planar main body constructed of a material imparting flexibility at or near a transverse center axis, said transverse center axis dividing said planar main body into a first end portion sized to simultaneously retract both cheeks when inserted into a person's mouth, thereby maintaining said person's mouth in an open position and a second end portion sized to simultaneously retract both cheeks when inserted into a person's mouth, thereby maintaining said person's mouth in an open position; said first end portion having a geometrical shape or outline that is the same as a geometrical shape or outline of said second end portion, said first side having a first reflective surface at said first end portion, a second reflective surface at said second end portion, and a non-reflective surface separating said first reflective surface and said second reflective surface; said opposing second side having a non-reflective surface;
    said first end portion having a first vertical side edge arranged in a parallel orientation relative to said transverse center axis and comprising a first pair of opposing curved surfaces separated by a first protuberance;
    said second end portion having a second vertical side edge arranged in a parallel orientation relative to said transverse center axis and comprising a second pair of opposing curved surfaces separated by a second protuberance; and
    each of said first and second end portions having a pair of longitudinal side edges having inwardly directed surfaces which form arcuate indentations at or about said transverse center axis.

2. The dual sided dental instrument for use in intraoral photography according to claim 1 wherein said first end portion and said second end portion have different sizes or dimensions.

3. The dual sided dental instrument for use in intraoral photography according to claim 1 wherein said first and second reflective surfaces include a reflective material attached to said first end portion and said second end portion, respectively.

4. The dual sided dental instrument for use in intraoral photography according to claim 3 wherein said reflective material is a mirror.

5. The dual sided dental instrument for use in intraoral photography according to claim 1 wherein said non-reflective surface is constructed of a plastic material which provides a black matte finish.

6. The dual sided dental instrument for use in intraoral photography according to claim 1 wherein said first end portion is hingedly attached to said second end portion.

7. The dual sided dental instrument for use in intraoral photography according to claim 6 wherein one of said first or second end portions pivots with respect to other one of said first or second end portions at least 90 degrees in a plurality of directions.

8. The dual sided dental instrument for use in intraoral photography according to claim 1 wherein said first end portion is slidably attached to said second end portion.

9. The dual sided dental instrument for use in intraoral photography according to claim 1 wherein said planar main body is constructed of a material that can be sterilized.

10. The dual sided dental instrument for use in intraoral photography according to claim 1 wherein said first reflective surface and said second reflective surface contain an adhesive coating having reflective properties.

11. A dual sided dental instrument for use in intraoral photography comprising:
   a main body having a reflective side and an opposing non-reflective side, said main body having a transverse center axis dividing said main body into a first end portion and a second end portion, said first end portion sized and shaped to simultaneously retract both cheeks when inserted into a person's mouth, thereby maintaining said person's mouth in an open position, said second end portion sized and shaped to simultaneously retract both cheeks when inserted into a person's mouth, thereby maintaining said person's mouth in an open position; said first end portion having a geometrical shape or outline that is the same as a geometrical shape or outline of said second end portion;
   said reflective side having a first reflective surface at said first end, a second reflective surface at said second end, and a non-reflective surface there between;
   said first end portion having a first vertical side edge arranged in a parallel orientation relative to said transverse center axis and comprising a first pair of opposing curved surfaces separated by a first protuberance;
   said second end portion having a second vertical side edge arranged in a parallel orientation relative to said transverse center axis and comprising a second pair of opposing curved surfaces separated by a second protuberance.

12. The dual sided dental instrument for use in intraoral photography according to claim 11 wherein at least a portion of said planar main body is flexible.

* * * * *